(12) United States Patent
Pagan

(10) Patent No.: US 6,463,927 B1
(45) Date of Patent: Oct. 15, 2002

(54) MEDICAL TUBE ASSEMBLIES

(75) Inventor: Eric Pagan, Kent (GB)

(73) Assignee: Smiths Group PLC, London (GB)

( * ) Notice: Subject to any disclaimer, the term of this patent is extended or adjusted under 35 U.S.C. 154(b) by 0 days.

(21) Appl. No.: 09/037,995

(22) Filed: Mar. 11, 1998

(30) Foreign Application Priority Data

Mar. 27, 1997 (GB) .............................................. 9706372

(51) Int. Cl.$^7$ ............................................. A61M 16/00
(52) U.S. Cl. ............................. 128/200.26; 128/207.14
(58) Field of Search ....................... 128/200.26, 207.14, 128/207.15, 207.29; 600/585

(56) References Cited

U.S. PATENT DOCUMENTS

| | | | | | |
|---|---|---|---|---|---|
| 229,633 A | * | 7/1880 | Pfarre | | |
| 2,463,149 A | * | 3/1949 | Caine | ................... | 128/200.26 |
| 2,862,498 A | * | 12/1958 | Weekes | ................. | 128/207.14 |
| 3,508,554 A | * | 4/1970 | Sheridan | ................ | 128/207.14 |
| 3,754,554 A | * | 8/1973 | Felbarg | ................. | 128/200.26 |
| 3,802,440 A | * | 4/1974 | Salem et al. | ................. | 600/585 |
| 3,906,938 A | * | 9/1975 | Fleischhacker | ............. | 600/585 |
| 3,957,055 A | * | 5/1976 | Linder et al. | .......... | 128/200.26 |
| 3,996,939 A | | 12/1976 | Sheridan | ................. | 128/207.15 |
| 4,444,185 A | * | 4/1984 | Shugar | ................... | 128/200.26 |
| 4,449,522 A | * | 5/1984 | Baum | ................... | 128/200.26 |
| 4,454,887 A | * | 6/1984 | Kruger | ....................... | 128/772 |
| 4,529,400 A | * | 7/1985 | Sholten | ................ | 128/207.14 |
| 4,589,410 A | | 5/1986 | Miller | .................... | 128/207.15 |
| 4,593,687 A | * | 6/1986 | Gray et al. | ............ | 128/200.26 |
| 4,607,635 A | * | 8/1986 | Heyden | ................... | 128/207.15 |
| 4,637,388 A | * | 1/1987 | Melendy | ................ | 128/207.14 |
| 4,637,389 A | * | 1/1987 | Heyden | ................ | 128/207.15 |
| 4,655,214 A | * | 4/1987 | Linder | ................... | 128/207.14 |
| 4,949,716 A | * | 8/1990 | Chenoweth | ............ | 128/200.26 |
| 4,960,122 A | * | 10/1990 | Mizus | .................... | 128/200.26 |
| 5,007,434 A | * | 4/1991 | Doyle et al. | ................. | 600/585 |
| 5,058,577 A | * | 10/1991 | Six | ........................ | 128/200.26 |
| 5,095,915 A | * | 3/1992 | Engelson | ................ | 600/585 |
| 5,106,381 A | * | 4/1992 | Chikama | .................... | 600/585 |
| 5,358,479 A | * | 10/1994 | Wilson | ........................ | 600/585 |
| 5,383,852 A | | 1/1995 | Stevens-Wright | ............ | 604/95 |
| 5,392,791 A | * | 2/1995 | Nyman | ........................ | 600/585 |
| 5,406,960 A | * | 4/1995 | Corso, Jr. | .................... | 600/585 |
| 5,437,288 A | * | 8/1995 | Schwartz et al. | ............ | 600/585 |
| 5,507,279 A | * | 4/1996 | Fortune et al. | ......... | 128/200.26 |
| 5,546,937 A | * | 8/1996 | Stuart et al. | ............ | 128/200.26 |
| 5,728,148 A | * | 3/1998 | Bostrom et al. | ............ | 600/585 |

FOREIGN PATENT DOCUMENTS

| | | |
|---|---|---|
| GB | 1479396 | 7/1977 |
| GB | 2312378 A | 10/1997 |

\* cited by examiner

*Primary Examiner*—Aaron J. Lewis
(74) *Attorney, Agent, or Firm*—Connolly Bove Lodge & Hutz, LLP

(57) ABSTRACT

A guide for an endotracheal tube has an outer sheath of a flexible plastics within which is embedded a bendable rod. The rod is of a metal, such as a copper-plated, zinc-iron alloy and is crimped with a series of indentations along opposite sides so as to give it a preferential plane of bending including the center lines of the indentations. The sheath is a hollow tube opening at both ends through hollow plugs.

14 Claims, 2 Drawing Sheets

MEDICAL TUBE ASSEMBLIES

BACKGROUND OF THE INVENTION

This invention relates to medical tube assemblies.

The invention is more particularly concerned with medical tube assemblies that can be bent and set to a desired shape.

It is often desirable to be able to bend a medical tube guide to a particular shape, such as, to facilitate introduction of the medical tube. Bendable guides or stylets are presently available including a metal rod encased in a plastic sheath. Guides of a plastics material are also available, such as described in GB2312378. Conventional guides can be bent equally easily in any plane, so that different parts of the guide can be bent in different planes. This can be a disadvantage in some applications, such as where introducing an endotracheal tube, because there is a risk that the guide might be inadvertently bent at an angle away from the path along which the tube is to be introduced. Where using a conventional guide in such an application, care must be taken to ensure that it is only bent in one plane, so that this can be aligned with the path of introduction. There is also a problem with guides that can be bent in more than one plane, in that it increases the risk that the plastic sheath on the guide will be creased or kinked where it is bent. It can also be an advantage, in some cases, to be able to bend the tube itself to a particular shape.

BRIEF SUMMARY OF THE INVENTION

It is an object of the present invention to provide an improved medical tube assembly.

According to one aspect of the present invention there is provided a medical tube assembly comprising a medical tube and a rod extending within a sheath of a flexible plastics material, the rod being of a different material from the sheath and the rod being bendable to a set bend and being preferentially bendable in one plane.

The rod with the sheath may be removably inserted within the bore of the medical tube as a guide member. The sheath may be of tubular form with a bore extending along its length, the rod extending within the wall of the sheath. The guide member may have a plug inserted in one end of the sheath, the plug having a bore therethrough communicating with the bore through the sheath.

Alternatively, the sheath may be provided by a wall of the medical tube, the rod being embedded in the wall.

The medical tube is preferably an endotracheal tube.

According to another aspect of the invention there is provided a tracheal tube assembly including a tubular member of a flexible plastics material having a first end for location in the trachea and a second end for location outside the body, the tubular member having an inflatable cuff extending around it towards the first end such that the tubular member can be sealed with the patient's trachea by inflating the cuff, the assembly including a rod of a different material extending within the wall of said tubular member along its length, and the rod being bendable to a set bend and being preferentially bendable in one plane so that the tracheal tube assembly can be bent to a desired shape.

The rod is preferably of a metal such as zinc-iron alloy, and may be plated with copper. The rod preferably is formed with a series of indentations along opposite sides, the center lines of the indentations lying in the plane. The indentations may be formed by crimping.

Endotracheal tube assemblies according to the present invention, will now be described, by way of example, with reference to the accompanying drawings.

DETAILED DESCRIPTION OF THE PREFERRED EMBODIMENTS

Figure 1:
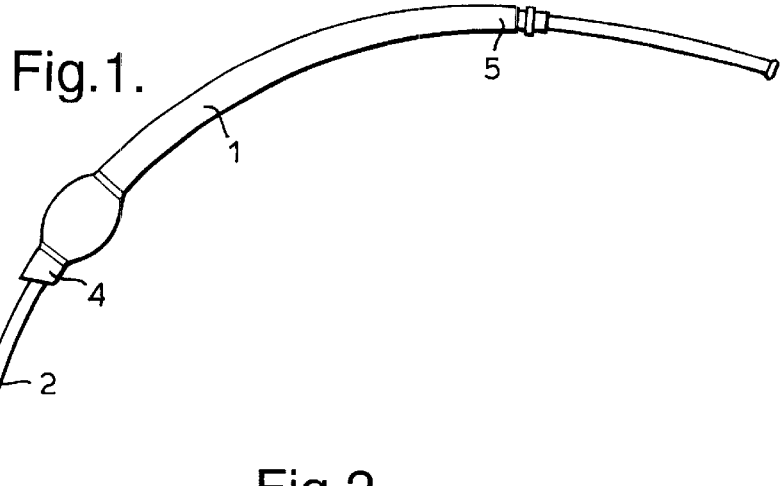
FIG. 1 is a side elevation view of the assembly including a guide.

With reference first to FIG. 1, the assembly comprises a conventional endotracheal tube 1 and a guide 2 extending along the main bore of the tube and projecting from both the patient end 4 and the machine end 5 of the tube.

Figures 2, 4:
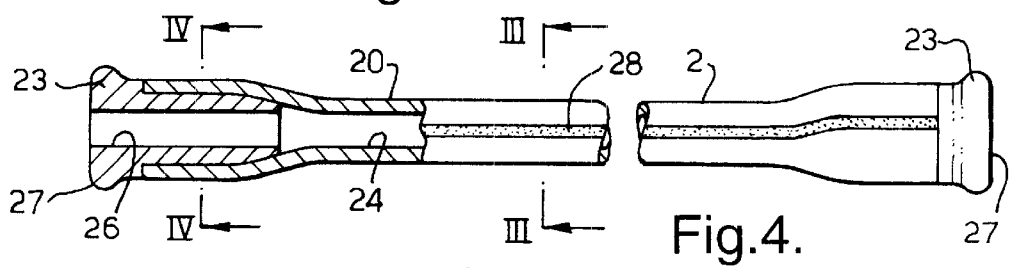
FIG. 2 is an enlarged, partly-sectional side elevation view of the guide.
FIG. 4 is a transverse sectional view of the guide along the line IV—IV.
Figure 3:
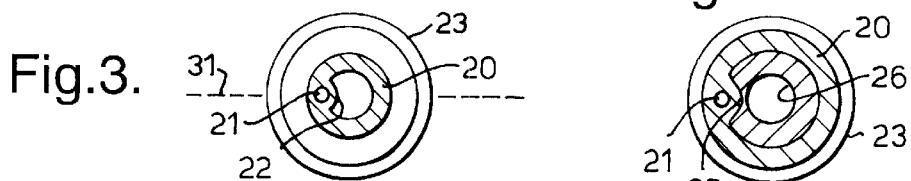
FIG. 3 is a transverse sectional view of the guide along the line III—III.

With reference now also to FIGS. 2 to 4, the guide 2 includes a flexible, plastics tube 20, such as of PVC, and a bendable metal rod 21 extending along the length of the tube within its wall. The wall of the tube 20 is thickened in the region of the rod 21 to form an internally-projecting rib 22, the guide 2 being typically 500 mm or 700 mm long with an external diameter of about 5 mm. At opposite ends of the guide 2, two hollow plugs 23 are inserted in and bonded to the bore 24 through the tube 20. The plugs 23 have an external keyway 25 oriented to align with the rib 22 and have a bore 26 extending therethrough in communication with the bore 24 through the tube 20. The plugs 23 have enlarged, rounded outer ends 27 to form atraumatic ends to the guide 2. A coloured stripe 28 extends along the length of the guide 2 extruded in the wall of the tube 20 directly above the rod 21, so as to indicate the location of the rod.

Figures 5, 6:
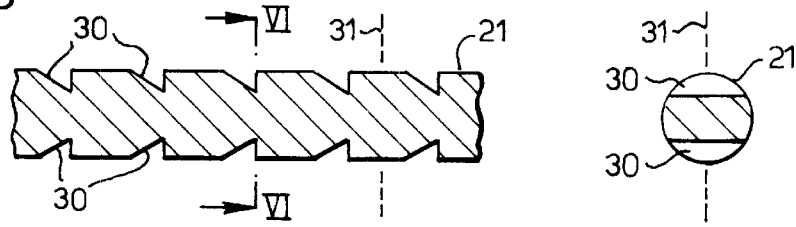
FIG. 5 is an enlarged sectional side elevation view of the rod member in the guide.
FIG. 6 is a transverse sectional view of the rod member along the line VI—VI of FIG. 5.
Figure 7:
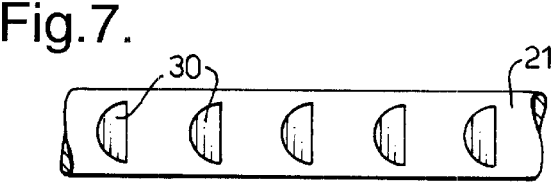
FIG. 7 is a plan view of the rod member.

With reference now also to FIGS. 5 to 7, the metal rod 21 is of a zinc-iron alloy plated on its surface with a layer of copper. The rod 21 is of circular shape in section, with a diameter of about 1mm, but the rod is formed with two series of indentations 30 of triangular shape along opposite sides, the indentations being spaced from one another by a distance of about 2 mm. The indentations are formed by applying a crimping tool to opposite sides of the rod 21 along an axis 31. In the indentations 30, the rod 21 has a flattened, almost rectangular section so that the rod can bend preferentially about the thickness of the indented regions. The indentations, therefore, give the rod 2 1a preferential plane of bending, namely the plane including the centre lines of the sides of the rod along which the indentations 30 are formed. The force required to bend the rod in its preferential plane of bending is less than that required to bend it in other planes. When bent in the preferential plane of bending, the two series of indentations 30 extend along the inside and outside of the bend of the rod 21. The metal rod 21 is available from Rehau AG & Co of Erlangen, Germany. The rod 21 is embedded within the plastics material of the wall of the tube 20 so that the plastics material fills the spaces formed by the indentations 30 and provides a secure retention of the rod, even after repeated bending of the guide. The orientation of the rod 21 is such that the crimping axis 31 is aligned with a diameter of the tube 20, so that the preferential plane of bending of the guide 2 lies on a diameter of the tube that includes the metal rod 21. The guide 2 is preferably made by continuously extruding the plastics tube 20 about the metal rod 21, which is fed into the extruder from reel stock.

The bore 24 through the guide 2 enables it to be used for ventilation, oxygen administration, gas monitoring or the like. A bronchoscope could alternatively be inserted to extend along the bore 24.

The guide 2 may be used to introduce an endotracheal tube. The guide 2 is first bent to the desired shape, in the plane indicated by the stripe 28, and is inserted into the trachea of the patient until the patient end extends through the vocal chords. The bore 24 through the guide 2 may help provide a preliminary air path in cases of upper airway obstruction. The endotracheal tube 1 is then slid on the machine end of the guide 2, in the manner shown in FIG. 1, and is pushed along the guide through the vocal chords. When the correct location has been reached, the cuff on the tracheal tube is inflated and the guide is removed by pulling out rearwardly, leaving the tube 1 in position.

The guide 2 may also be used to exchange one endotracheal tube for another. The guide is inserted along the bore of an endotracheal tube that is already in position in the patient. The endotracheal tube is then removed by sliding along the guide, which is left in position. A new endotracheal tube is then slid into the patient along the guide.

The guide 2 can be easily bent in a single plane without any special precautions being taken. This is a particular advantage because it enables the guide to be bent to shape quickly, thereby reducing the time taken for the intubation procedure.

Various modifications to the guide are possible. For example, the bendable rod member need not be crimped but it could be given a preferential plane of bending in other ways, such as, for example, by having a cross section that is smaller in one dimension so that the rod preferentially bends in that direction. The rod could, for example, be of rectangular section. The rod member need not be made of a metal but could, for example, be made of a plastics material that can be bent to take a set bend. The rod could, for example, be a crimped plastics rod.

Figure 8:
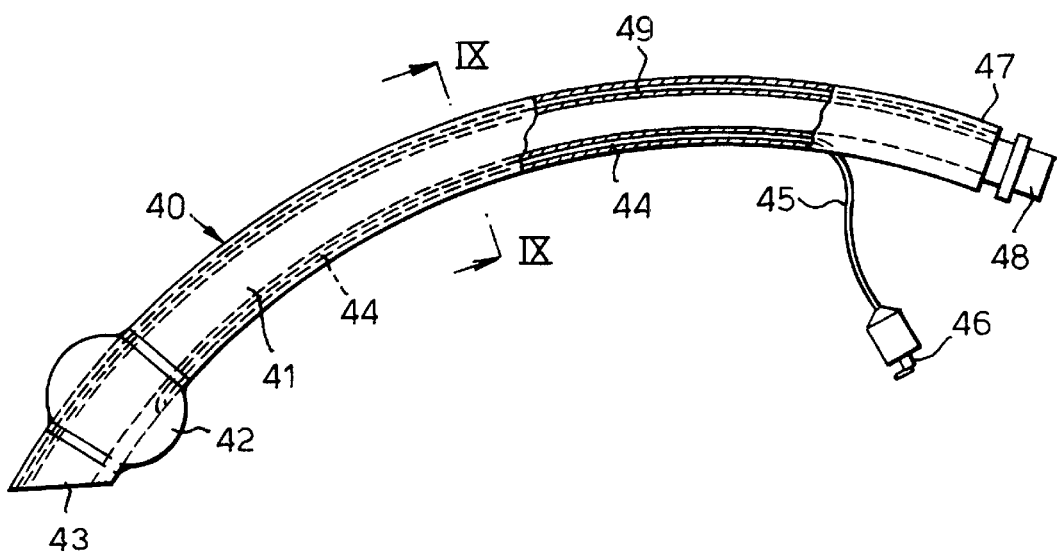
FIG. 8 is a partly-sectional side elevation view of an alternative endotracheal tube including a bendable rod within its wall.
Figure 9:
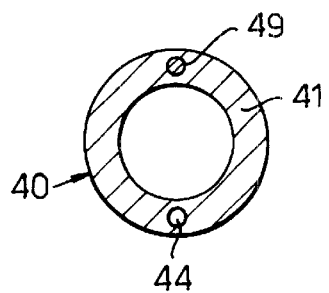
FIG. 9 is a transverse sectional view of the tube of FIG. 8, to an enlarged scale, along the line IX—IX.

In another arrangement, as shown in FIGS. 8 and 9, an endotracheal tube or assembly 40 has a tubular shaft 41 of a flexible plastics material, such as PVC, with an inflatable cuff 42 extending around it close to its patient end 43. The cuff 42 is inflated to seal with the patient's trachea via an inflation lumen 44 extending within the wall of the shaft 41, which is connected to an inflation line 45 and a connector 46. The opposite, machine end 47 of the tube 40 is adapted, in use, to project from the patient's mouth and is terminated with a connector 48 by which the tube can be connected to a breathing circuit, not shown. The tube 40 also includes a crimped metal rod 49 extending along its length within the wall of the shaft 41, which provides a sheath for the rod. The rod 49 may be the same as the rod 21 described above with reference to FIGS. 1 to 7. The tube 40 has a natural curvature along its length, as in conventional endotracheal tubes, the rod 49 being located to extend along the outside of the bend of the curve and oriented so that its preferential plane of bending is the same as the plane of natural curvature of the tube. When the clinician wishes to modify the shape of the tube, such as to ease intubation or to conform more closely to the anatomy of the patient, he can bend the tube 40 by hand, with the rod 49 retaining the desired bend. The preferential plane of bending of the rod reduces the risk that the tube will be bent to one side, away from the natural plane of bending of the tube. The tube 40 can be introduced using the guide 2 described above, if desired.

The tube 40 may be manufactured in various different ways, such as by co-extruding the shaft about the rod 49.

What I claim is:

1. A medical tube assembly comprising:
    a medical tube;
    a bendable rod of circular cross section,
        said cross section having a diameter with first and second ends,
        said rod having a preferred plane of bending defined parallel to said diameter and extending along the length of said rod,
        said first and second ends defining first and second sides of said rod;
    a first array of indentations extending along said first side of said rod;
    a second array of indentations extending along said second side of said rod, said first and second arrays cooperating to confer on said rod said preferred plane of bending, and
    a flexible, plastic sheath encasing said rod wherein said sheath has an inner wall in contact with the surface of said rod, said inner wall having crenellations interdigitating with and in contact with said indentations of said rod; wherein
    said rod is formed from a material different from said sheath, said rod is manually bendable to a set bend co-planar with said preferred plane of bending, and wherein said rod retains said set bend.

2. An assembly according to claim 1, wherein said rod with said sheath is removably inserted within a bore of said medical tube, and wherein said member is a guide member for said tube.

3. An assembly according to claim 2, wherein said sheath is of tubular form with a bore extending along its length, and wherein said rod extends within a wall of said sheath.

4. An assembly according to claim 3, wherein said guide member includes a plug inserted in one end of said sheath, and wherein said plug has a bore therethrough communicating with said bore through said sheath.

5. An assembly according to claim 1 wherein said sheath is provided by a wall of said medical tube, and wherein said rod is embedded in said wall.

6. An assembly according to claim 1, wherein said medical tube is an endotracheal tube.

7. An assembly according to claim 1, wherein said rod is of a metal.

8. An assembly according to claim 7, wherein said rod is of a zinc-iron alloy.

9. An assembly according to claim 7, wherein said rod is plated with copper.

10. An assembly according to claim 1, wherein said rod comprises a series of bilaterally opposed indentations, and wherein said indentation are coplanar with said preferred plane of bending.

11. An assembly according to claim 10, wherein said indentations are formed by crimping.

12. A medical tube assembly, according to claim 1, wherein said rod is manually bendable in said preferred plane of bending to a set bend, such that the assembly can be bent to, and hold, a desired shape.

13. An assembly according to claim 12, wherein said medical tube is an endotracheal tube.

14. A tracheal tube assembly comprising: a tubular member of a flexible plastics material having a first end for location in the trachea and a second end for location outside the body, said tubular member having an inflatable cuff extending around it towards said first end such that said tubular member can be sealed with a patient's trachea by inflating said cuff and a rod of a different material extending within a wall of said tubular member along its length, wherein said rod has a centerline and has a non-circular cross section at a plurality of locations along its length wherein said non-circular cross sections impart a preferred plane of bending co-planar with said centerline, and wherein said rod is manually bendable in said preferred plane of bending to a set bend such that said tracheal tube assembly can be bent to a desired shape.

* * * * *